United States Patent [19]

McKinnie

[11] Patent Number: 5,235,000
[45] Date of Patent: Aug. 10, 1993

[54] PREPARATION, STORAGE, AND USAGE OF BROMINE CHLORIDE

[75] Inventor: Bonnie G. McKinnie, Magnolia, Ark.

[73] Assignee: Ethyl Corporation, Richmond, Va.

[21] Appl. No.: 625,087

[22] Filed: Dec. 10, 1990

[51] Int. Cl.[5] .................. C07C 17/12; C07C 17/14
[52] U.S. Cl. .................................. 525/355; 570/200; 570/206; 568/316; 568/323; 568/437; 525/333.4
[58] Field of Search .............. 570/206, 200; 423/349, 423/498; 525/354, 355; 568/316, 323, 437

[56] References Cited

U.S. PATENT DOCUMENTS

| | | | |
|---|---|---|---|
| 2,662,855 | 12/0000 | Kamiet | 210/28 |
| 3,845,146 | 10/1974 | Moore et al. | 570/206 |
| 4,352,909 | 10/1982 | Barda et al. | 525/157 |
| 4,832,873 | 5/1989 | Favstritsky et al. | 252/601 |

OTHER PUBLICATIONS

Cotton, et al., Advanced Inorganic Chemistry, 2nd Ed. Interscience Publishers, New York, 1966, pp. 329–330.

Primary Examiner—Marianne M. Cintins
Assistant Examiner—Kimberly J. Kestler
Attorney, Agent, or Firm—David E. LaRose

[57] ABSTRACT

This invention relates to a process for reducing the formation of carbonyl halide in bromine chloride and to an improved process for the bromination of compounds with BrCl in the presence of a carbonyl halide poisonable catalyst.

14 Claims, 2 Drawing Sheets

PREPARATION, STORAGE, AND USAGE OF BROMINE CHLORIDE

BACKGROUND

This invention relates to a process for reducing the formation of carbonyl halide in bromine chloride. The process may be employed during the production and/or storage of bromine chloride.

Bromine chloride is well known as a bromination agent and as a water treatment chemical. Moore, et al. U.S. Pat. No. 3,845,146, discloses the bromination of benzene, lower alkyl benzene, phenol, biphenyl and diphenyl oxide with bromine chloride in the presence of iron or a Friedel-Crafts catalyst. The resultant brominated products are useful as flame retardants. Barda, et al., U.S. Pat. No. 4,352,909, discloses that polystyrene can be nuclear brominated with bromine chloride in the presence of a chlorinated hydrocarbon solvent and a catalytic amount of a Lewis acid catalyst. The use of bromine chloride as a water treatment chemical is illustrated in U.S. Pat. No. 2,662,885.

While bromine chloride is safely used in commerce, its high reactivity argues well for care in its production, use and storage. Normally, bromine chloride is kept under a pad of a commercially available inert gas, e.g. nitrogen, argon, etc. While the use of such a pad prevents most undesirable reactions between the bromine chloride and its environs, it has been now been discovered that some bromine chloride will still contain, as an impurity, phosgene or carbonyl halide which cannot be attributable to the bromine chloride's method of manufacture. Thus, despite the use of prior art pads, the bromine chloride is still entering into an undesirable impurity producing reaction.

The presence of an impurity such as phosgene in the bromine chloride can severely limit the use of such bromine chloride in the manufacture of brominated organic compounds if the phosgene interferes with the manufacturing process. For example, in the bromination of aromatics, a carbonyl halide poisonable catalyst, such as a Friedel-Crafts catalyst, is used. Thus, the use of a bromine chloride which contains a carbonyl halide, such as phosgene, would result in catalyst poisoning and a resultant degradation of process efficiency. Due to the presence of carbonyl halide in most commercially available bromine chloride, many of today's catalyzed bromination reactions suffer from catalytic poisoning.

It is therefore an object of this invention to provide bromine chloride which is substantially free of carbonyl halide impurities.

It is another object of this invention to provide an improved process for the bromination of a compound with bromine chloride in the presence of a carbonyl halide poisonable catalyst.

SUMMARY OF THE INVENTION

This invention relates to a process for reducing the formation of carbonyl halide in bromine chloride and to an improved process for the bromination of compounds with BrCl in the presence of a carbonyl halide poisonable catalyst.

DESCRIPTION OF THE PREFERRED EMBODIMENTS

Figure 1:
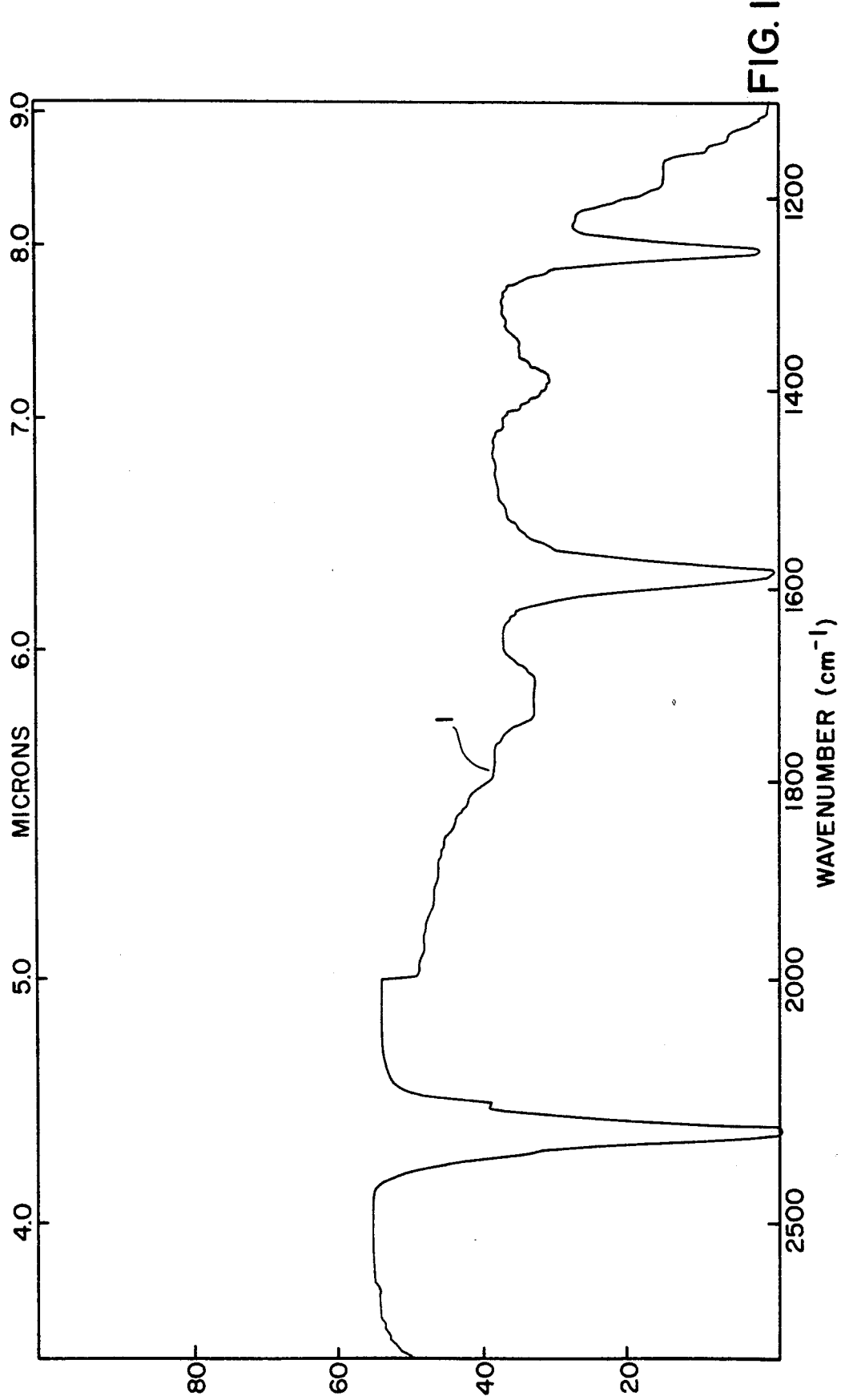
FIG. 1 is an infra red spectrograph of BrCl which is essentially free of carbonyl halide.

The process of this invention provides for the obtainment of bromine chloride which is essentially free of carbonyl halide and which, therefore, is particularly suitable for use in processes which utilize a catalyst that is normally poisoned by carbonyl halide. The process comprises; (a) producing, (b) storing, or (c) producing and storing bromine chloride under an inert atmosphere which is substantially free of carbon monoxide.

Bromine chloride which is essentially free of carbonyl halide is defined, for purposes of this invention, as BrCl containing less than about 100 ppm carbonyl halide, preferably less than about 50 ppm carbonyl halide, and most preferably less than about 30 ppm carbonyl halide.

The term "inert atmosphere" is meant to include any fluid which in and of itself does not react with the bromine chloride under the conditions in which the bromine chloride is produced and/or stored. The inert atmosphere is preferably a gas and is conveniently nitrogen, argon, helium, or dry air. Nitrogen is most preferred.

As above mentioned, the inert atmosphere is substantially free of carbon monoxide, i.e. the presence of carbon monoxide does not exceed about 200 ppm in the inert atmosphere. Preferably there is less than 20 ppm carbon monoxide in the inert atmosphere.

Production of the inert atmosphere so as to insure the substantial absence of carbon monoxide therein is easily achieved by generation of the inert atmosphere from an essentially pure liquid form of an inert gas. When the inert atmosphere is a gas such as nitrogen the carbon monoxide level is kept low by simply vaporizing the very pure liquid form of nitrogen in the substantial absence of carbon monoxide. For example when the gas is nitrogen, a suitable procedure comprises heating a stream of nitrogen liquid with ambient air as the nitrogen liquid passes through the tubes of a finned-tubed heat exchanger, the external surfaces of the tubes being exposed to air temperatures above the boiling point of liquid nitrogen.

It is theorized, though this invention is not limited by such theory, that even a minor amount of carbon monoxide in an inert gas will react with bromine chloride to form the undesirable carbonyl halide, e.g. phosgene and/or carbonyl dibromide, under storage, use and/or production conditions. While, it is known that substantially equimolar amounts of carbon monoxide and elemental $Cl_2$ react readily in the presence of an activated charcoal catalyst to form phosgene, and equimolar amounts of carbon monoxide and elemental $Br_2$ react much more slowly, it was surprising, and quite unexpected that BrCl would react with a gas containing only a minor amount of carbon monoxide. By a minor amount of carbon monoxide is meant that the amount of carbon monoxide in the gas is less than about 3,000 ppm carbon monoxide. Even a minor amount of carbon monoxide is sufficient to form an undesirable quantity of carbonyl halide in the BrCl product.

The bromine chloride of this invention may be prepared generally in accordance with a number of known methods with the improvement comprising producing, storing, or producing and storing the BrCl under an inert atmosphere which is substantially free of carbon monoxide.

To prepare the BrCl which is essentially free of carbonyl halide, a closed reaction vessel is first padded with the inert atmosphere which atmosphere is essentially free of carbon monoxide. Next, equal molar amounts of bromine and chlorine are mixed in the closed reaction vessel for 1–2 hours and the bromine chloride thus formed is withdrawn from the liquid phase in the vessel. It is highly desirable that dry $Br_2$ and $Cl_2$ (<30 ppm $H_2O$) be used since water not only can contribute to the formation of hydrohalic acid, but a BrCl product containing water may more quickly deactivate many catalysts.

In one embodiment, this invention provides a BrCl composition comprising a predominate amount of BrCl and a lesser amount of impurities, said impurities comprising less than about 100 ppm carbonyl halide. Preferably the amount of carbonyl halide in the BrCl composition is less than about 50 ppm and most preferably, less than about 30 ppm.

In another embodiment, this invention provides an improved process for the production of brominated compounds, e.g. brominated aromatics, brominated cycloaliphatics, brominated aliphatics etc., which are formed in the presence of a carbonyl halide poisonable catalyst. The improvement comprises, during and/or subsequent to the production of the BrCl, maintaining an inert atmosphere over the BrCl, the inert atmosphere being substantially free of carbon monoxide whereby the formation of carbonyl halide in the BrCl is greatly reduced.

In this preferred embodiment the nucleus of an aromatic compound is polybrominated generally in accordance the process disclosed in Moore et al., U.S. Pat. No. 3,845,146, incorporated herein by reference as if fully set forth.

The aromatic compound to be polybrominated may be benzene, a lower alkyl benzene having one or two alkyl groups of 1–6 carbon atoms, biphenyl or diphenyl oxide. Of these aromatic compounds, benzene, and toluene are preferred, with benzene being especially preferred.

Carbonyl halide poisonable catalysts which may be used with this invention are, at least initially, in the form of $AlCl_3$, $AlBr_3$, $AlI_3$, $AlCl_3 \cdot RNO_2$, $AlBr_3 \cdot RNO_2$, $BBr_3$, $BCl_3$, $BF_3$, $BI_3$, $BeCl_2$, $BiCl_3$, $CdCl_2$, $FeCl_2$, $FeCl_3$, $FeBr_3$, $GaCl_2$, $GaBr_3$, $GaCl_3$, $GaI_3$, $GaCl_3$-$RNO_2$, $HfBr_4$, $HfCl_4$, $HfI_4$, $InBr_3$, $InCl_3$, $InI_3$, $MoCl_5$, $MoF_6$, $NbCl_5$, $NbF_5$, $PtCl_4$, $ReCl_3$, $ReCl_5$, $SbCl_5$, $SbCl_3$, $SbF_5$, $SbF_5$—$RNO_2$, $SnBr_4$, $SnCl_4$, $TaBr_5$, $TaCl_5$, $TaF_5$, $TiBr_4$, $TiCl_4$, $UCl_4$, $WCl_6$, $ZrCl_4$, $ZnCl_2$, or mixtures thereof. Preferably the carbonyl halide poisonable catalyst is a Lewis acid catalyst, and most preferably is $AlBr_3$, $AlCl_3$, $BBr_3$, $BCl_3$, $BF_3$, $BeCl_2$, $BiCl_3$, $CdCl_2$, $FeCl_3$, $GaBr_3$, $GaCl_3$, $SbCl_5$, $SbCl_3$, $SnCl_4$, $SnBr_4$, $TiCl_4$, $UCl_4$, $ZrCl_4$, $ZnCl_2$, or mixtures thereof.

During the preparation of the polybrominated aromatic compound, the aromatic nucleus is contacted with bromine chloride in an amount at least stoichiometric to give the desired product, in the presence of carbonyl halide poisonable catalyst, at a temperature of from about −10° to about 150° C., and under essentially autoqenous pressure. It is a key feature of this invention, that during and/or subsequent to the production of the bromine chloride reactant, an inert atmosphere, which is substantially free of carbon monoxide, is maintained over the BrCl whereby the formation of carbonyl halide in BrCl is greatly reduced.

To prepare the polybrominated aromatic compound generally in accordance with U.S. Pat. No. 3,845,146, the carbonyl halide poisonable catalyst and one of the reactants are added to a batch reactor and then the other reactant is slowly added. Either the aromatic compound or the essentially carbonyl halide free bromine chloride ma be initially charged into the reactor along with the catalyst. The BrCl reactant which is charged to the reactor is preferably prepared, stored, and used in an atmosphere which is substantially free of carbon monoxide.

Once the reactants have been charged to the reactor, the reaction vessel is closed so as to obtain an essentially autogenous pressure. The autogenous pressure encountered in the reaction vessel during the course of the reaction may vary widely. Suitably, these pressures may range from about 10 to about 200 psig or more, with pressures of from about 50 to about 100 psig being preferred. During the reaction, the vessel may be vented to control the pressure within a desirable range.

The temperature of the reaction is not critical. Generally, the temperatures may range from about −10° to about 150° C. or more, with temperatures of less than 50° C. being preferred.

A solvent may be used in the reaction although good conversion and yields are obtained by using excess bromine chloride as the solvent. Suitable solvents include the halogenated hydrocarbons such as methylene chloride, chloroform, carbon tetrachloride, ethylene dichloride, methylene bromide and the like.

It is most desirable that the bromination reaction be run under essentially anhydrous conditions. It is well known, that water tends to deactivate the catalyst and causes the reaction to proceed at a much slower rate.

The reaction time required varies widely as different reactant ratios, temperatures, pressures and solvents are employed. Generally, essentially complete bromination is obtained within a few hours.

In still another preferred embodiment this invention provides an improved process for the production of nuclear brominated polystyrene generally in accordance the process disclosed in Barda et al., U.S. Pat. No. 4,352,909, incorporated herein by reference as if fully set forth.

The process for making brominated polystyrene generally in accordance with U.S. Pat. No. 4,352,909, comprises:

1. charging a solvent, preferably a chlorinated aliphatic hydrocarbon, to a reaction vessel that is equipped for mechanical agitation;

2. dissolving polystyrene having a molecular weight of at least 20,000 in the solvent; and 3. reacting the dissolved polystyrene with an amount of essentially carbonyl halide free bromine chloride in excess of the stoichiometric amount of bromine chloride required for achieving the desired degree of bromination in the presence of up to about 15% by weight of the polystyrene of a carbonyl halide poisonable catalyst.

The polystyrene reactant which is brominated by the process of this invention may have any desired molecular weight, but it is preferably a styrene polymer or oligomer having a molecular weight of 20,000 or more. The polystyrene reactant may be halo-substituted or lower alkyl-substituted. It may also be a copolymer of styrene and alpha-methyl styrene, or a block copolymer of polystyrene and one or more polymers of the saturated hydrocarbyl type.

As noted above, it is a key feature of this invention, that during and/or subsequent to the production of the bromine chloride reactant, an inert atmosphere, which is substantially free of carbon monoxide, is maintained over the BrCl whereby the formation of carbonyl halide in BrCl is greatly reduced. Preferably the bromine chloride reactant is chilled prior to its addition to the reaction vessel and added gradually over a period of several hours or more.

Catalyst useful in the process of this invention may be any one or more of the beforementioned carbonyl halide poisonable catalysts. Of the beforementioned catalyst, an antimony chloride, antimony bromide, aluminum chloride, or aluminum bromide is more preferred with antimony trichloride being the most preferred. The catalyst may be added to the polystyrene solution or to the BrCl solution or to both.

Best results in the reaction are obtained when the catalyst is maintained under essentially anhydrous conditions. One means for drying a catalyst which has not been maintained under such anhydrous conditions is by rinsing the catalyst with a suitable solvent, then heating to drive off an azeotrope of water and excess solvent.

During the addition of the BrCl reactant, the temperature of the solution in the reactor is maintained within a controlled range, generally in a range of from about 20° C. to about 50° C. The reaction goes forward at lower temperatures but at a slower rate. It also goes forward at higher temperatures, but the color of the product may be dark. When the BrCl addition is complete, the reaction mixture is continuously stirred for another period of time, sufficient to permit the reaction to go to completion.

After the reaction is essentially complete, any excess BrCl is destroyed, as by the addition of an aqueous solution of an alkali or an alkali metal bisulfite. Agitation of the reaction mixture is then stopped and phase separation between the resulting organic layer and the aqueous layer occurs.

Product recovery can be accomplished by mixing the organic layer with non-solvent liquid, such as an alkanol, to precipitate the product. The preferred technique involves the use of methanol. In this technique, the methanol or other nonsolvent liquid, that is miscible with the organic liquid in which the reaction product is dissolved, is maintained in a separate vessel at close to the boiling point. The contents of the reaction vessel are heated to about 80° C., and then slowly added to the heated alkanol, as it is agitated. The brominated polymer precipitates in the form of fine particles, which can be recovered by filtration, and dried as in a forced air oven at about 115° C.

The process of U.S. Pat. No. 4,352,909 is also effective for the bromination of substituted polystyrene, the substitution being along the alkylene chain of the polystyrene, or nuclear. Examples include: poly-(monobromostyrene); poly(monochloro-styrene); poly-(dichlorostyrene); poly-(monochloro-monobromostyrene); poly-(2-methyl styrene); poly-(alpha-methyl styrene); and poly-(mono-lower alkyl styrene).

Example I is an illustration of the preferred process of this invention for preparing BrCl which is substantially free of carbonyl halide.

EXAMPLE I

In a 100 ml Fisher-Porter tube with a magnetic stirrer and Kynar ® top was placed 94.2 grams of commercially available bromine. The tube was previously purged with dry air containing less than 100 ppm carbon monoxide. Chlorine (43.0 grams) was fed in under autogenous pressure giving liquid BrCl. Analysis by infrared spectroscopy (I.R.) through a 20 mm cell indicated an absorbance of 0.02 at 1800 cm-1, i.e. no significant amount of $COCl_2$, $COBr_2$, or $COBrCl$ was detected, point 1 in FIG. 1.

In order to illustrate a means for detection and identification of carbonyl halide in BrCl, the following example is given.

EXAMPLE II

Figure 2:
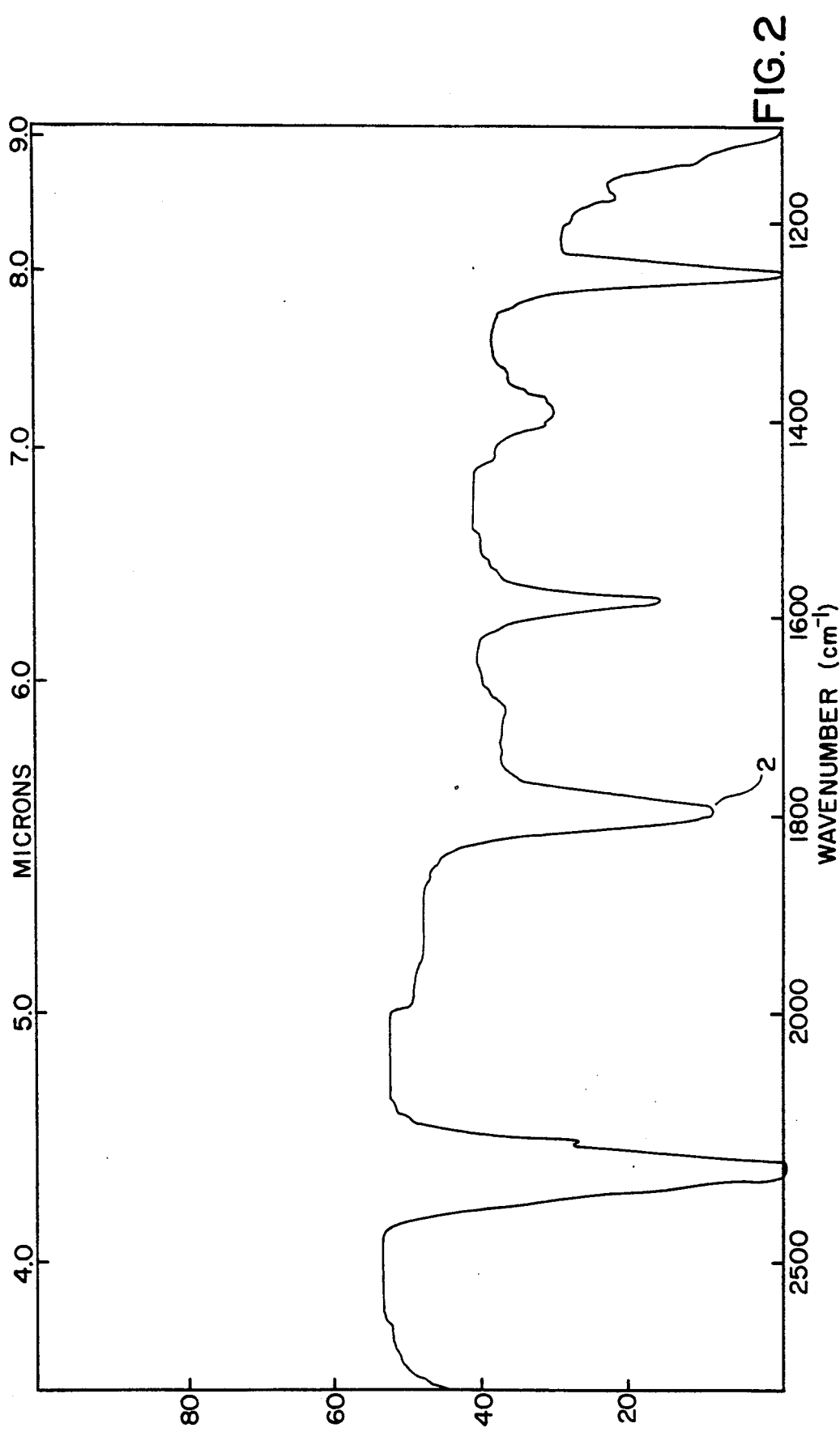
FIG. 2 is an infra red spectrograph of BrCl containing an undesirable amount of carbonyl halide.

In a 100 mL Fisher-Porter tube with a magnetic stirrer and a Kynar ® top, BrCl product from Example I was pressured to 80 psig with carbon monoxide, and held at this pressure for about 45 seconds. At the end of this period of time the pressure was vented until the mixture started to boil. The liquid BrCl was then analyzed by I.R. in a 20 mm cell which indicated an absorbance of 0.67 at 1,800 cm-1, point 2 in FIG. 2.

As is clearly shown in the above examples and FIGURES, when the bromine chloride product is exposed to carbon monoxide, a significant absorption band is noted at 1,800 $cm^{-1}$, indicating the presence of carbonyl halide. However, when the BrCl product is kept substantially free of carbon monoxide, the absorbance peak at 1,800 $cm^{-1}$ is not prevalent. This indicates a marked reduction in the amount of carbonyl halide present in the BrCl product. Since there is little or no carbonyl halide in the BrCl, the degree of poisoning of the Lewis acid catalyst is greatly reduced.

In accordance with the foregoing, this invention is susceptible to considerable variation within the spirit and scope of the appended claims.

I claim:

1. In a process for brominating an aromatic, cycloaliphatic, or aliphatic compound with BrCl in the presence of a carbonyl halide poisonable catalyst, the improvement comprising: during and/or subsequent to the production of said BrCl, maintaining an inert atmosphere over said BrCl, said inert atmosphere containing no more than 200 ppm carbon monoxide whereby the formation of carbonyl halide in said BrCl is less than about 100 ppm.

2. The process of claim 1 wherein the aromatic compound to be brominated is benzene, a lower alkyl benzene having one or two alkyl groups of 1-6 carbon atoms, biphenyl or diphenyl oxide.

3. The process of claim 1 wherein the aromatic compound to be brominated is benzene or toluene.

4. The process of claim 1 wherein the catalyst is a Lewis acid catalyst.

5. The process of claim 1 wherein the aromatic compound is benzene and the catalyst is a Lewis acid catalyst.

6. The process of claim 5 wherein the inert atmosphere is nitrogen and wherein said nitrogen is vaporized from a liquid nitrogen source.

7. The process of claim 1 wherein the inert atmosphere is nitrogen, or argon.

8. The process of claim 1 wherein the inert atmosphere is nitrogen.

9. The process of claim 1 wherein the inert atmosphere is nitrogen and wherein said nitrogen is vaporized from a liquid nitrogen source.

10. In a process for brominating polystyrene with BrCl in the presence of a carbonyl halide poisonable catalyst, the improvement comprising: during and/or subsequent to the production of said BrCl, maintaining an inert atmosphere over said BrCl, said inert atmosphere containing no more than 200 ppm carbon monoxide whereby the formation of carbonyl halide in said BrCl is less than about 100 ppm.

11. The process of claim 10 wherein the polystyrene is a styrene polymer or oligomer having a molecular weight of 20,000 or more.

12. The process of claim 11 wherein the polystyrene is a halo-substituted or lower alkyl-substituted polystyrene.

13. The process of claim 11 wherein the carbonyl halide poisonable catalyst is a Lewis catalyst.

14. The process of claim 13 wherein the catalyst is $SbCl_3$.

* * * * *